United States Patent [19]

Trick

[11] 4,417,567

[45] Nov. 29, 1983

[54] ARTIFICIAL SPHINCTER

[75] Inventor: Robert E. Trick, Racine, Wis.

[73] Assignee: Medical Engineering Corporation, Racine, Wis.

[21] Appl. No.: 322,285

[22] Filed: Nov. 17, 1981

Related U.S. Application Data

[63] Continuation-in-part of Ser. No. 292,051, Aug. 12, 1981, Pat. No. 4,386,601.

[51] Int. Cl.³ .............................................. A61B 17/00
[52] U.S. Cl. .................................... 128/1 R; 128/346; 128/DIG. 25
[58] Field of Search ............... 128/1 R, 346, DIG. 25; 138/30

[56] References Cited

U.S. PATENT DOCUMENTS

| | | | |
|---|---|---|---|
| 3,863,622 | 2/1975 | Buuck | 128/1 R |
| 4,167,201 | 9/1979 | Zahid | 138/30 |
| 4,222,377 | 9/1980 | Burton | 128/1 R |

OTHER PUBLICATIONS

Kintzonidis et al.—Trans. Amer. Soc. Art. Internal Organs—vol. XVII, 1971 pp. 138–142.

Primary Examiner—Dalton L. Truluck
Attorney, Agent, or Firm—Quarles & Brady

[57] ABSTRACT

An artificial sphincter comprises a closed hydraulic system which includes an inflatable occlusion means which is normally inflated with hydraulic fluid under pressure to cut off flow through a body passage. An accumulator balloon having a relatively inelastic shell serves as a reservoir for hydraulic fluid for the inflatable occlusion means and includes a gas filled bladder within the inelastic shell to maintain a constant pressure in the system. The system also contains a pump to suck fluid from the occlusion means to deflate it and open the body passage to fluid flow and tubing connecting the inflatable occlusion means, the accumulator balloon and the pump to complete a closed system. The sphincter also includes a pressure intensifier which temporarily increases the pressure in the occlusion means to compensate for an anticipated increase in fluid pressure in the body passage. The pressure intensifier includes a source of pressurizing fluid which can be actuated in anticipation of the increase in fluid pressure in the body passage to deliver an increased volume of fluid under pressure to the occlusion means and to operate a pressure actuated shut-off valve which prevents the loss of fluid from the occlusion means.

5 Claims, 4 Drawing Figures

ARTIFICIAL SPHINCTER

RELATED APPLICATION

The present application is a continuation-in-part of my earlier copending patent application Ser. No. 292,051 filed Aug. 12, 1981, now U.S. Pat. No. 4,386,601, issued June 7, 1983.

FIELD OF THE INVENTION

The present invention relates to an improved artificial sphincter for reversibly closing a body passage to fluid flow. More particularly, it relates to artificial sphincter with a pressure intensifier which prevents the loss of continence due to a fluid pressure increase such as might be caused by a cough, sneeze or other pressure inducing event.

BACKGROUND OF THE INVENTION

Many persons have non-functioning or malfunctioning sphincters which because of congenital malformations, trauma to the sphincter nerves or muscles, or disease of the sphincter nerves or muscles to make it impossible for them to control the discharge of body waste.

One of the most troublesome and embarrassing conditions is the malfunctioning of the urethral sphincter. The urethral sphincter retains urine in the bladder until the sphincter is relaxed which permits the urine to be discharged. As a result of the malfunctioning of the urethral sphincter, uncontrolled drainage of urine from the body can occur. Obviously, this can be embarrassing to the individual and can restrict his activities.

Attempts have been made in the past to provide an artificial sphincter which can serve as a substitute for a malfunctioning urethral sphincter or provide means for controlling artificial openings that have no natural sphincters.

In my earlier copending patent application Ser. No. 292,051, I disclosed and described an improved artificial sphincter for reversibly closing body passages. The artificial sphincter of my earlier application although superior to those employed in the past did not include any means of preventing the incontinence which can result from an increase in urine pressure as the result of a cough, sneeze or the like.

SUMMARY OF THE INVENTION

It is an object of the present invention to provide a novel artificial sphincter for effectively and reversibly closing a body passage which includes means for preventing incontinence due to temporary or transitory sharp increases in fluid pressure in the body passage.

It is a further object to disclose an artificial sphincter with an improved accumulator balloon assembly.

The artificial sphincter of the present invention comprises a closed hydraulic system which includes an inflatable occlusion means which is normally inflated with hydraulic fluid under pressure to cut off flow through a body passage; an accumulator balloon having a relatively inelastic shell which serves as a reservoir for hydraulic fluid for the inflatable occlusion means and a gas filled bladder within the inelastic shell; a pump to suck fluid from the occlusion means to deflate it and open the body passage to fluid flow and tubing connecting the inflatable occlusion means, the accumulator balloon and the pump to form a closed system. The sphincter has a first check valve at the inflatable occlusion means which allows fluid to freely flow out of the inflatable occlusion means, a second check valve at the accumulator balloon which allows fluid to freely flow into the accumulator balloon and resistance means which restricts fluid flow into the inflatable occlusion means and out of the accumulator balloon to a low rate of flow. The sphincter also includes a pressure intensifier which temporarily increases the pressure in the occlusion means to compensate for an anticipated increase in urine pressure.

In a preferred embodiment, the pressure intensifier includes a source of pressurizing fluid which can be actuated in anticipation of an increase in fluid pressure in the body passage to deliver an increased volume of fluid under pressure to the occlusion means and to operate a pressure actuated shut-off valve which prevents the loss of fluid from the occlusion means.

In another embodiment, the gas filled bladder of the balloon accumulator has an elongated stem which has its free end closed with a one way valve or resealable member and can be conveniently implanted under the user's skin to facilitate easy reading and adjusting of occluding pressure.

BRIEF DESCRIPTION OF THE DRAWINGS

The invention will be hereinafter more fully described with reference to the accompanying drawings in which.

DESCRIPTION OF THE PREFERRED EMBODIMENT

Figure 1:
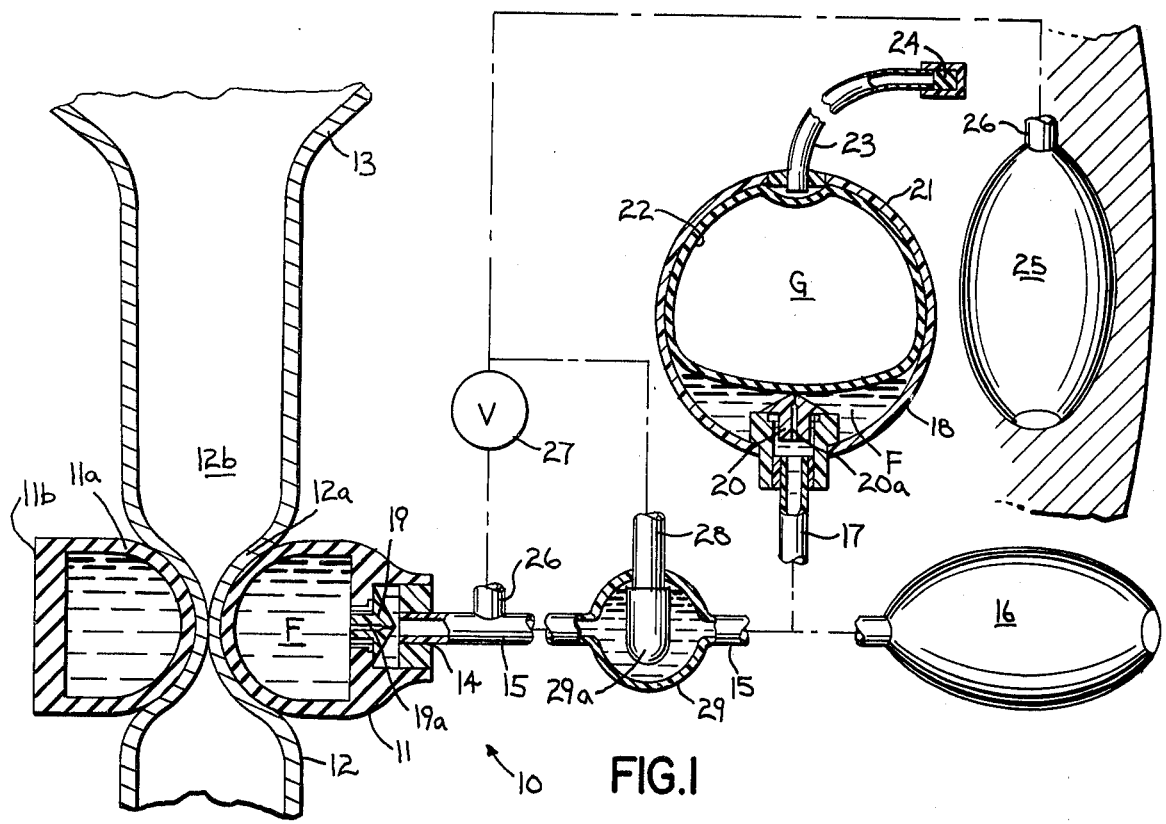
FIG. 1 is a view, partly in section, a preferred embodiment of the artificial sphincter of the present invention with the body passage closed.
Figure 2:
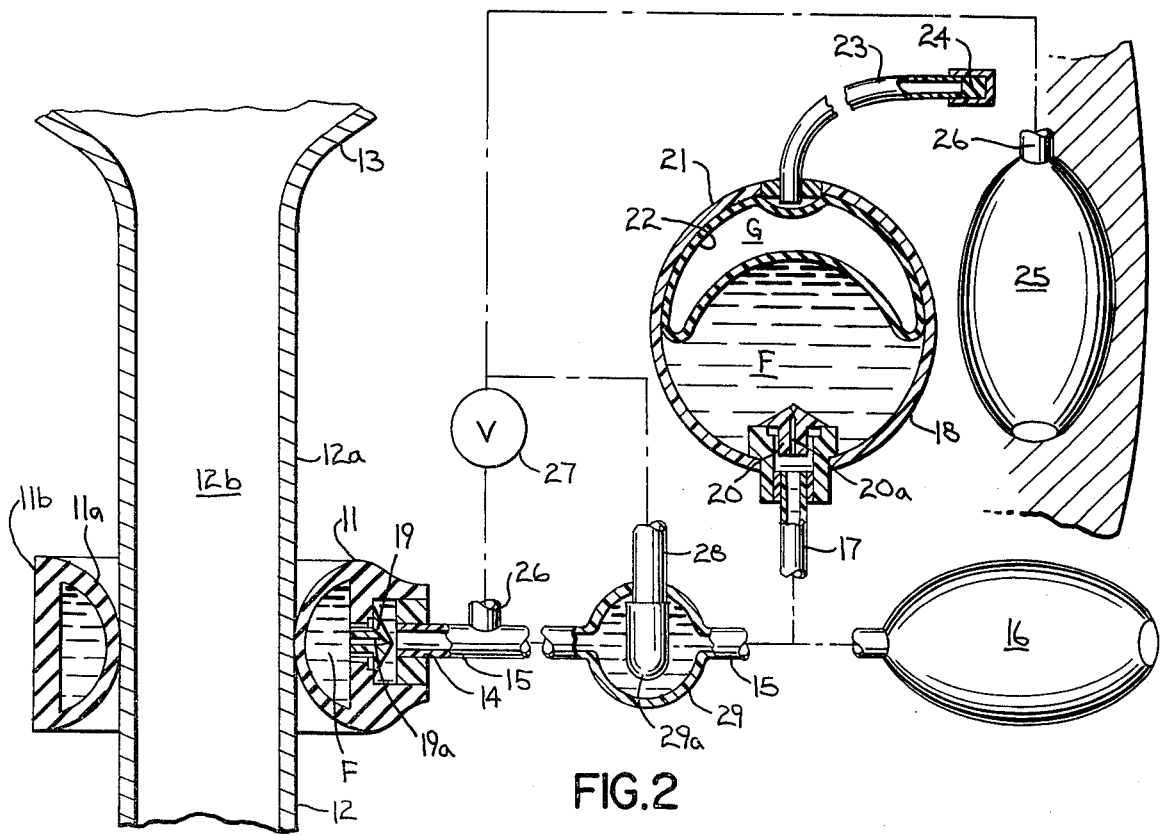
FIG. 2 is a view similar to FIG. 1 with the body passage open.
Figure 3:
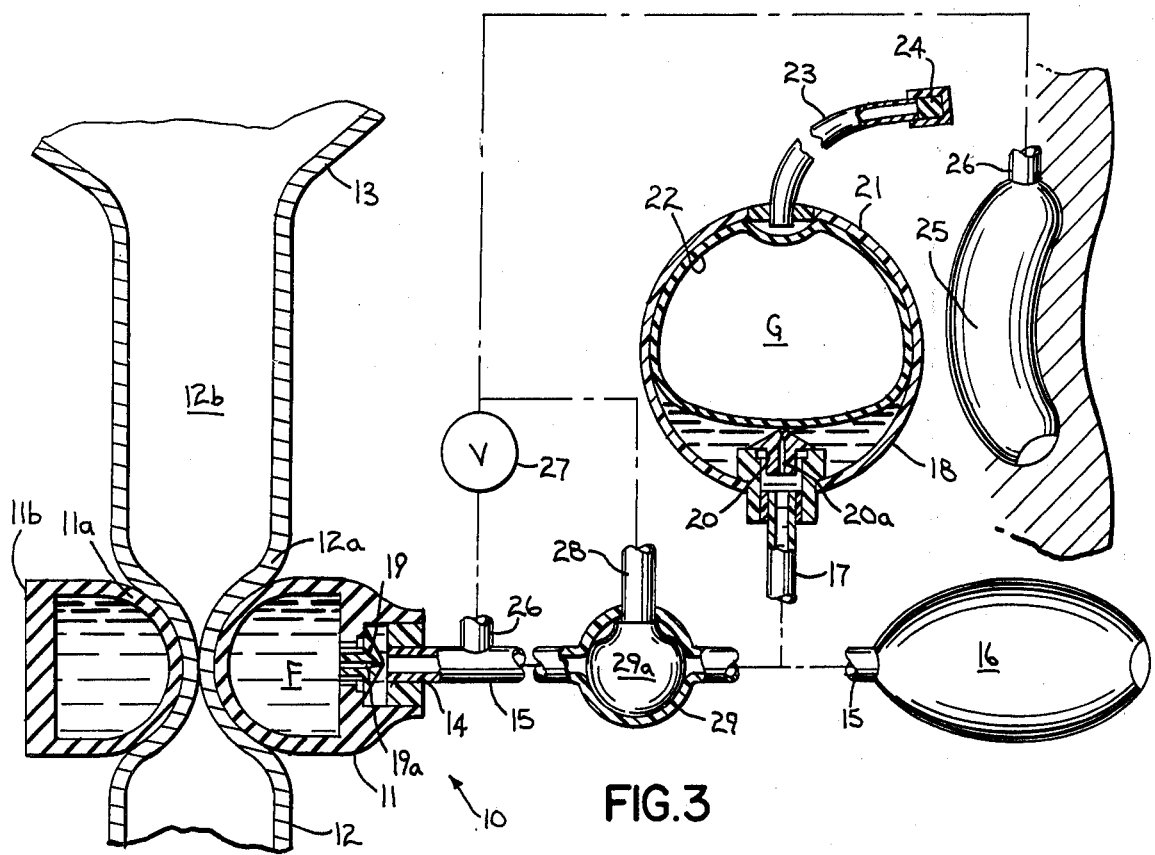
FIG. 3 is a view similar to FIG. 1 with the pressure intensifier of the artificial sphincter activated.

The preferred embodiment of the artificial sphincter of the present invention seen in FIGS. 1 to 3 is generally designated 10. As seen therein, an inflatable cuff 11 of the sphincter 10 is positioned about an urethra 12 leading from a bladder 13. The natural urethra normally is opened or closed by one or more sphincters which are controlled by voluntary nerve impulses.

The inflatable cuff 11 has a port 14 which is connected by tubing 15 to a pressure pump 16. A branch 17 in the tubing 15 leads to an accumulator balloon 18. Both the cuff 11 and the accumulator balloon 18 are equipped with combination check/resistance valves 19 and 20, respectively. The check/resistance valve 19 allows the free flow of fluid out of the cuff 11 and restricts flow into the cuff 11 to a low rate of flow. The check/resistance valve 20 allows the free flow of fluid into the accumulator balloon 18 and resists flow out to a low rate of flow. The combined check/resistance valves 19 and 20, if desired, could be replaced by a separate check valve and resistance means.

As seen in the drawings, the preferred accumulator balloon 18 has a relatively thick inelastic shell 21 which contains a closed gas filled bladder 22 provided with an elongated stem 23 which is closed with a resealable valve or septum 24 through which gas can be added or removed from the bladder 22 with a hollow needle (not shown).

The actual closing and opening of the urethra 12 is accomplished by inflating the cuff 11 to collapse the wall 12a of the urethra 12 and close the lumen 12b (as seen in FIG. 1). Although the cuff 11 is inflatable, it does not have to be elastic as the term is normally understood. However, it is necessary that the cuff 11 have a readily deformable inner wall 11a. The deformable wall 11a is preferably thinner and thus more elastic and deformable than the outer wall 11b. However, it will be appreciated that the difference in deformability of the walls 11a and 11b can be achieved by other techniques than varying the thickness, e.g. making wall 11b of a less flexible material.

The operation of the artificial sphincter 10 which controls the flow of fluid through the urethra 12 now will be described in connection with FIGS. 1 and 2.

The cuff 11 is normally inflated as seen in FIG. 1 causing the wall 12a of the urethra 12 to be collapsed closing the lumen 12b. When it is desired to empty the bladder 13, the cuff 11 is deflated to permit the natural resiliency of the wall 12a of the urethra to cause the lumen 12b to open. The cuff 11 which is normally inflated can be deflated by repeatedly stroking the pump 16 to suck fluid F out of the cuff 11. As the cuff 11 is rapidly emptied of fluid it deflates and the lumen 12b of the urethra opens. When the pump 16 is stroked the fluid F sucked from the cuff 11 is forced by the pump 16 via the tubing 15 and 17 into the shell 21 of the accumulator balloon 18. As the shell 21 of the accumulator balloon 18 fills with fluid F, the gas G in the bladder 22 is compressed to occupy less space within the shell 21 in order to accommodate the additional fluid F from the cuff 11 and pump 16. When the cuff 11 is fully open the bladder 22 and accumulator balloon 18 are in the state seen in FIG. 2. The refilling or reinflation of the cuff 11 which commences immediately when the pump 16 is not stroked is delayed by the resistance means, i.e. openings 19a and 20a of valves 19 and 20. The resistance openings 19a and 20a allow the fluid F to slowly leak back into the cuff 11 at a low rate of flow. During the slowed refilling of the cuff 11, the bladder 13 is emptied. The refilling of the cuff 11 begins automatically once the stroking of the pump 16 stops because the gas in bladder 22, which has been compressed by the fluid F forced into the shell 21 by the pump 16, starts to expand to its maximum size. As the bladder 22 expands, the fluid F in the shell 21 leaks through the resistance opening 20a and passes via the tubing 17 and 15 and the resistance opening 19a into the cuff 11 causing it to reinflate and collapse and close the lumen 12b.

The accumulator balloon 18 with its elongated stem 23 closed by the septum 24 is an improvement on the balloon accumulator, which was described and claimed in my earlier patent application Ser. No. 292,051. The balloon accumulators of my earlier application and the present application both provide more constant pressure and are longer lasting than the previously employed accumulating devices which were usually simple elastic silicone balloons which depended upon their wall thickness and the quantity of fluid they contained to maintain pressure within desired ranges. After extended use the prior art silicone balloons tended to take a set causing pressure control to degrade and necessitating replacement of the system.

The shell 21 of the accumulator balloon 18 is inelastic under conditions of use and the gas filled bladder 22 establishes the working pressure of the sphincter. The bladder 22 is made of an elastomer which does not allow the gas to diffuse into the fluid and it is sized and shaped so that it is under negligible stress and no pressure differential exists between the gas and fluid.

In the balloon accumulator disclosed in my patent application Ser. No. 292,051, the gas pressure in the gas bladder is adjusted by penetrating the septum on the balloon with a hollow needle to add or remove gas. In contrast, as seen in FIG. 1 of the present application the bladder 22 has an elongated stem 23 which is closed with a resealable valve or septum 24. The length of the stem 23 is such that it permits the balloon 18 with its bladder 22 to be implanted in the abdominal cavity of a patient and the free end of the stem 23 with its septum 24 to be implanted at a convenient location under the patient's skin thus making possible the easy reading and adjusting of the occluding pressure.

The novel pressure intensifier of the present invention will now be described in connection with FIGS. 1, 2 and 3. As seen therein, the pressure intensifier system includes a second pressure pump 25, a length of tubing 26 connecting the pressure pump 25 to the cuff 11; a free flow/resistance valve 27 located along the tubing 26 between the pump 25 and the cuff 11, a branch 28 of tubing 27 located between the pump 25 and the free flow/resistance valve 27 leading to a pressure actuated valve 29 which is operatively connected in tubing 15 between pressure pump 16 and cuff 11. The valve 27 provides a resistance to fluid flow to cuff 11 which generates a back pressure when fluid is forced from the pump 25 towards the cuff 11 but allows the free flow of fluid from the cuff 11 to the pump 25. The back pressure generated by the valve 27 causes fluid to flow along branch 28 to the pressure actuated valve 29 causing it to be activated.

Figure 4:
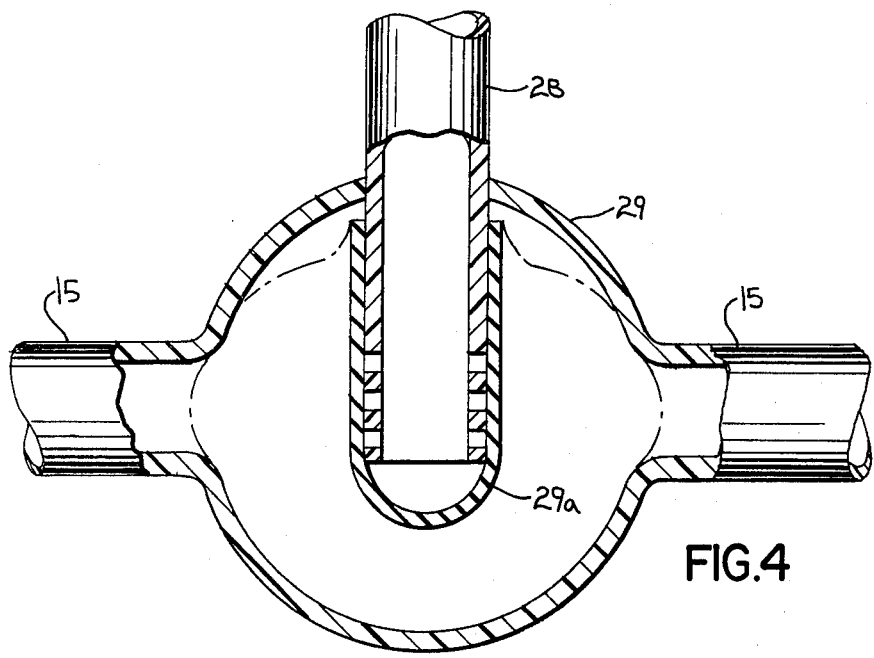
FIG. 4 is an enlarged view, partly in section, of the pressure actuated valve of the pressure intensifier of the artificial sphincter of FIG. 1.

The pump 25 of the pressure intensifier system is implanted under the user's skin at a convenient location. When a cough, sneeze, or other phenomena that might result in increased fluid pressure in the body passage 12 or the bladder 13 is anticipated, the pressure pump 25 is compressed as shown in FIG. 3. When the pressure pump 25 is compressed, fluid F under pressure leaves the pump 16 and flows toward the cuff 11. Fluid entering the valve 27 meets resistance creating a back pressure which results in fluid being preferentially directed via the branch 28 to the pressure actuated valve 29 causing the balloon 29a to expand and shut off fluid flow between the cuff 11 and the pressure pump 16. In FIG. 4, the valve 29 is shown with the balloon 29a in both its relaxed state and inflated state (phantom lines). Once the balloon 29a is inflated, all the fluid F leaving the pressure pump 25 is directed through the valve mechanism 27 to the cuff 11 causing an increased pressure therein to compensate for the anticipated increase of fluid pressure in the body passage or urethra 12. When the anticipated increase in fluid pressure in the urethra 12 has passed or no longer exists, the pressure on the pump 25 is relieved. The excess fluid F in the cuff 11 then flows freely back through the valve 27 to the pump 25 and the balloon 29a of the pressure actuated valve 29 deflates as the fluid F that was therein flows via tubing 26 to the pump 25. The artificial sphincter system components are then once again in the position seen in FIG. 1.

Prior to implanting the artificial sphincter components are connected together to form a fluid-tight system and the system is initially filled with hydraulic fluid under a slight pressure. The fluid preferred for this purpose is physiological saline. Other hydraulic fluids may be used but they should be physiologically compatible with body tissue and body organs in the event that a leak would develop in the system. Once implanted, adjustments in the pressure of the system are conveniently made through the septum 24 of the stem 23 of the bladder 22. If additional hydraulic fluid is needed it can be added through an addible on the pump bulb 16.

The components of the sphincter of the present invention are preferably made of medical grade polymer such as silicone rubber, and the fluid-tight connections between the various components are preferably made with an implantable grade of silicone adhesive of which several types are commercially available.

The apparatus of the present invention preferably is implanted completely within the patient's body. This may be done by making a suitable incision through the skin so as to provide access to the abdominal cavity. With the abdominal cavity opened, the urethra can be exposed and the cuff properly positioned. The pumps 16 and 25 which may take other forms than the pressure bulbs shown should then be arranged where they can be operated from the outside and the abdominal cavity surgically closed. The manner of the implantation described is generic for both males and females. The systems disclosed are sufficiently versatile to allow implanting in various regions of the body. For example, for male patients it may be preferable to implant the pump 16 in the patient's scrotum and the pump 25 in the abdomen just beneath the skin, or vice versa.

It will be appreciated by those skilled in the art that the foregoing description of the preferred embodiments for use in controlling the urethra has been for purposes of illustration only as the apparatus and the method of the present invention can be used to control flow through other body passages such as the colon. Therefore, it is intended that the scope of the invention not be limited except by the claims which follow.

I claim:

1. In an artificial sphincter for controlling the flow of fluid through a body passage which comprises an inflatable occlusion means which is normally inflated with hydraulic fluid to close the body passage, a source of pressurizing fluid for keeping the occlusion means inflated, pump means for sucking hydraulic fluid from the inflatable occlusion means to cause it to deflate and the body passage to open, and tubing connecting the pump means to the inflatable occlusion means and to the source of pressurizing fluid to form a closed system; the improvement which comprises pressure intensifying means for increasing the pressure in the occlusion means and preventing a temporary increase in fluid pressure in the body passage from causing fluid to leak past the occlusion means, said pressure intensifying means comprising a normally open pressure actuated valve for cutting off flow from the occlusive means to the pump means and the source of pressurizing fluid and a second pump means containing pressurizing fluid and operatively connected by a second length of tubing to both the pressure actuated valve and the occlusion means so that when said second pump means is operated both additional fluid is introduced into the occlusion means to increase the pressure therein and the pressure actuated valve is closed to prevent the additional fluid from leaving the occlusion means until the increased pressure is no longer needed.

2. The artificial sphincter of claim 1 in which the pressure intensifying means includes a second valve located in the second length tubing between the second pump means and the occlusive means, said second valve generating a back pressure when the second pump means is operated thus causing pressurizing fluid to flow to and close the pressure actuated valve.

3. The artificial sphincter of claim 1 in which the second pump means is a pressure bulb.

4. In an implantable artificial sphincter for controlling fluid flow through a body passage, said sphincter comprising an inflatable occlusion means for closing off the body passage, a source of pressurizing fluid for keeping the occlusion means normally inflated at a predetermined pressure to keep the body passage collapsed and closed, a length of tubing connecting the occlusion means to the source of pressurizing fluid and a pump operatively connected in the tubing between the occlusion means and the source of pressurizing fluid for sucking fluid from the occlusion means thus causing it to deflate and the body passage to open, the improvement which comprises pressure intensifying means for increasing the pressure in the occlusion means thus preventing a temporary increase in the fluid pressure in the body passage from causing fluid to leak past the occlusion means, said pressure intensifying means comprising a second pump containing pressurizing fluid, a second length of tubing connecting the second pump to the occlusion means, a branch in the second length of tubing and a normally open pressure actuated valve which is operatively connected to the first length of tubing between the occlusion means and the first pump and the source of pressurizing fluid, said pressure actuated valve being closed by fluid pressure when the second pump is operated to introduce additional fluid into the occlusion means to increase the fluid pressure therein.

5. The artificial sphincter of claim 4 in which the pressure intensifying means includes a second valve located in the second length of tubing between the second pump and the occlusion means, said second valve permitting fluid to flow freely from the occlusion means to the second pump and providing a resistance to flow from the second pump to the occlusion means thus generating a back pressure when the second pump is operated which causes a portion of the pressurizing fluid from the second pump to flow through the branch and close the pressure actuated valve.

* * * * *